United States Patent [19]

Kaneko et al.

[11] Patent Number: 5,600,029
[45] Date of Patent: Feb. 4, 1997

[54] PROCESS FOR PRODUCING DL-TOCOPHEROLS AND INTERMEDIATES THEREFOR

[75] Inventors: Tatsuhiko Kaneko, Mishima-gun; Kenichi Kashiwa, Kobe, both of Japan

[73] Assignee: Takeda Chemical Industries, Ltd., Osaka, Japan

[21] Appl. No.: 398,176

[22] Filed: Mar. 2, 1995

[30] Foreign Application Priority Data

Mar. 9, 1994 [JP] Japan .................................. 6-038380

[51] Int. Cl.$^6$ ...................................................... C07C 33/048
[52] U.S. Cl. ............................................................ 568/873
[58] Field of Search .............................................. 568/873

[56] References Cited

U.S. PATENT DOCUMENTS 5,136,061  8/1992  Takano et al. ........................... 549/512

*Primary Examiner*—Ba K. Trinh
*Attorney, Agent, or Firm*—Wenderoth, Lind & Ponack

[57] ABSTRACT

The present invention relates to a process for producing dl-tocopherols and intermediates for the production. dl-Tocopherols obtained by the present invention are useful compounds that are used as food additives, feed and medicaments.

1 Claim, No Drawings

PROCESS FOR PRODUCING DL-TOCOPHEROLS AND INTERMEDIATES THEREFOR

FIELD OF THE INVENTION

The present invention relates to a process for producing dl-tocopherols and intermediates for the production. dl-Tocopherols obtained by the present invention are useful compounds that are used as food additives, feed and medicaments.

BACKGROUND OF THE INVENTION

It has been known that dl-tocopherols, particularly dl-α-tocopherol, can be synthesized, for example, by reacting isophytol with trimethylhydroquinone as shown in the following scheme.

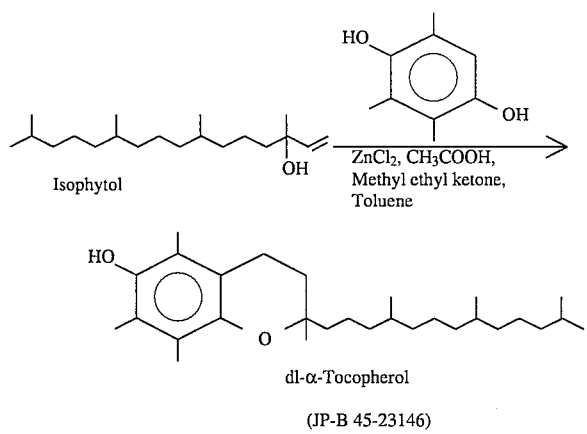

(JP-B 45-23146)

It has been known that isophytol used as the starting material in this reaction can be synthesized according to the following scheme.

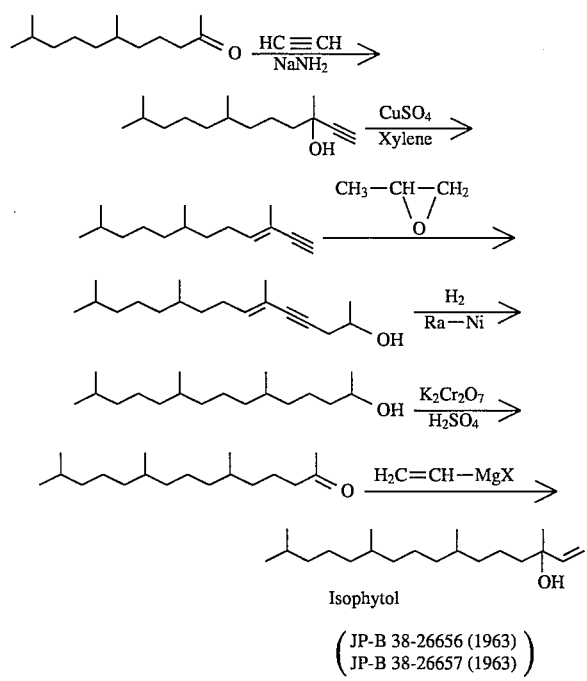

$$\begin{pmatrix} \text{JP-B 38-26656 (1963)} \\ \text{JP-B 38-26657 (1963)} \end{pmatrix}$$

In the above method, isophytol, which is an important starting material for the production of dl-tocopherols, is synthesized from 6,10-dimethylundecan-2-one ($C_{13}$ ketone) through many steps, in poor yield.

OBJECTS OF THE INVENTION

The main object of the present invention is to provide a process for readily producing dl-tocopherols in a few steps and high yield.

Another object of the present invention is to provide intermediates for the above production.

These objects as well as other objects and advantages of the present invention will become apparent to those skilled in the art from the following description.

SUMMARY OF THE INVENTION

The present invention provides a process for producing a compound of the formula (V):

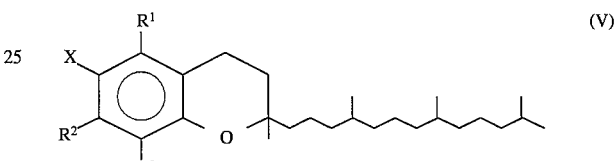

wherein $R^1$, $R^2$ and $R^3$ are each independently a hydrogen atom or an optionally substituted hydrocarbon group, and X is an optionally protected hydroxyl group, which comprises subjecting a compound of the formula (III):

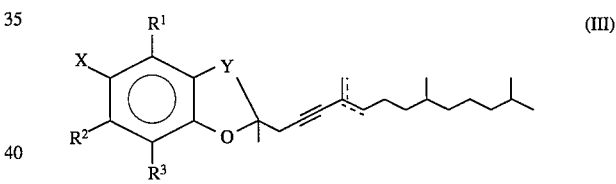

wherein $R^1$, $R^2$, and $R^3$ and X are as defined above, Y is —$CH_2$—$CH_2$—or —CH=CH—, and means that either of the two bonds is a double bond and the other is a single bond, to reduction reaction.

The present invention also provides a process for producing a compound of the formula (V):

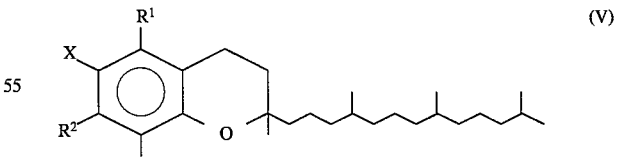

wherein $R^1$, $R^2$ and $R^3$ are each independently a hydrogen atom or an optionally substituted hydrocarbon group, and X is an optionally protected hydroxyl group, which comprises reacting a compound of the formula (II):

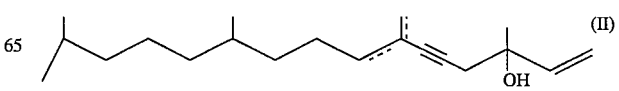

wherein means that either of the two bonds is a double bond and the other is a single bond, with a compound of the formula (VI):

(VI)

wherein $R^1$, $R^2$, $R^3$ and X are as defined above to obtain a compound of the formula (III'):

(III')

wherein the symbols are as defined above, and subjecting the compound of the formula (III') to reduction.

The present invention also provides a process for producing a compound of the formula (V):

(V)

wherein $R^1$, $R^2$ and $R^3$ are each independently a hydrogen atom or an optionally substituted hydrocarbon group, and X is an optionally protected hydroxyl group, which comprises subjecting a compound of the formula (IV):

(IV)

wherein $R^1$, $R^2$ and $R^3$ are as defined above, and means that either of the two bonds is a double bond and the other is a single bond, to ring-closure reaction to obtain a compound of the formula (III"):

(III")

wherein $R^1$, $R^2$, $R^3$, X and are as defined above, and subjecting the compound of the formula (III") to reduction.

The present invention also provides a process for producing a compound of the formula (II):

(II)

wherein means that either of the two bonds is a double bond and the other is a single bond, which comprises reacting a compound of the formula (I):

(I)

wherein is as defined above, with 2-methyl-2vinyloxirane.

The present invention also provides a compound of the formula (III):

(III)

wherein $R^1$, $R^2$ and $R^3$ are each independently a hydrogen atom or an optionally substituted hydrocarbon group, X is an optionally protected hydroxyl group, Y is —$CH_2$—$CH_2$— or —CH=CH—, and means that either of the two bonds is a double bond and the other is a single bond.

The present invention also provides a compound of the formula (III'):

(III')

wherein $R^1$, $R^2$ and $R^3$ are each independently a hydrogen atom or an optionally substituted hydrocarbon group, X is an optionally protected hydroxyl group, and means that either of the two bonds is a double bond and the other is a single bond.

The present invention also provides a compound of the formula (III"):

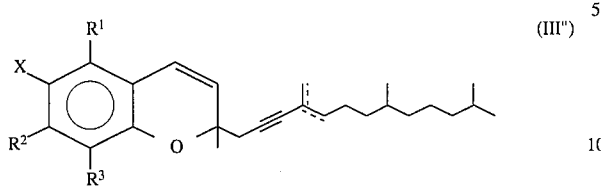
(III")

wherein $R^1$, $R^2$ and $R^3$ are each independently a hydrogen atom or an optionally substituted hydrocarbon group, X is an optionally protected hydroxyl group, and

means that either of the two bonds is a double bond and the other is a single bond.

The present invention also provides a compound of the formula (IV):

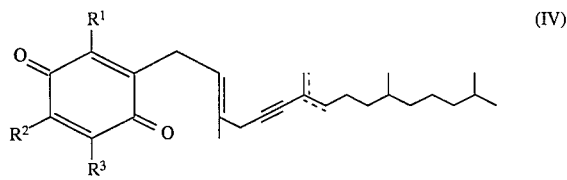
(IV)

wherein $R^1$, $R^2$ and $R^3$ are each independently a hydrogen atom or an optionally substituted hydrocarbon group, and

means that either of the two bonds is a double bond and the other is a single bond.

The present invention also provides a compound of the formula (II):

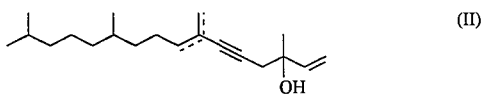
(II)

wherein

means that either of the two bonds is a double bond and the other is a single bond.

DETAILED DESCRIPTION OF THE INVENTION

The hydrocarbon group of the optionally substituted hydrocarbon group represented by $R^1$, $R^2$ or $R^3$ includes, for example, hydrocarbon groups having 1 to 20 carbon atoms. Examples of the hydrocarbon group include alkyl groups, alkenyl groups, alkynyl groups, aryl groups, aralkyl groups, etc.

The alkyl groups for the above hydrocarbon group are, for example, straight-chain or branched alkyl groups having 1 to 20 carbon atoms, preferably straight-chain or branched alkyl groups having 1 to 6 carbon atoms. Preferred examples of the alkyl groups include methyl, ethyl, propyl, isopropyl, butyl, sec-butyl, tert-butyl, pentyl, hexyl, etc. More preferred examples of the alkyl groups include straight-chain or branched alkyl groups having 1 to 3 carbon atoms such as methyl, ethyl, propyl, isopropyl, etc. In particular, methyl is preferred.

The alkenyl groups for the above hydrocarbon group are, for example, alkenyl groups having 2 to 20 carbon atoms, preferably alkenyl groups having 2 to 6 carbon atoms such as vinyl, allyl, 2-butenyl, methylallyl, 3-butenyl, 2-pentenyl, 4-pentenyl, 5-hexenyl, etc.

The alkynyl groups for the above hydrocarbon group are, for example, alkynyl groups having 2 to 20 carbon atoms, preferably alkynyl groups having 2 to 6 carbon atoms such as ethynyl, propargyl, 2-butyn-1-yl, 3-butyn-2-yl, 1-pentyn-3-yl, 3-pentyn-1-yl, 4-pentyn-2-yl, 3-hexyn-1-yl, etc.

The aryl groups for the above hydrocarbon group are, for example, aryl groups having 6 to 20 carbon atoms, preferably aryl groups having 6 to 14 carbon atoms such as phenyl, 1-naphthyl, 2-naphthyl, biphenylyl, anthryl, etc.

The aralkyl groups for the above hydrocarbon group are, for example, aralkyl groups having 7 to 20 carbon atoms, preferably aralkyl groups having 7 to 19 carbon atoms such as benzyl, phenethyl, benzhydryl, trityl, etc.

The hydrocarbon group may have at least one substituent. The number of the substituent is preferably 1 to 3. Examples of the substituent include alkoxy groups, acyloxy groups, alkoxycarbonyl groups, cyano group, oxo group, etc.

The alkoxy groups for the substituents include, for example, $C_{1-4}$ alkoxy groups such as methoxy, ethoxy, propoxy, butoxy, etc.

The acyloxy groups for the substituents include, for example, $C_{1-10}$ alkyl-carbonyloxy groups such as acetoxy, propionyloxy, butyryloxy, etc.; and $C_{6-10}$ aryl-carbonyloxy groups such as benzoyloxy, naphthoyloxy, etc.

The alkoxycarbonyl groups for the substituents include, for example, $C_{1-5}$ alkoxycarbonyl groups such as methoxycarbonyl, ethoxycarbonyl, propoxycarbonyl, butoxycarbonyl, etc.

Each of these substituents may have 1 to 3 appropriate substituents such as halogen, amino, etc.

The optionally protected hydroxyl group represented by X include, for example, a hydroxyl group and hydroxyl group protected with a protective group. The protective group of the protected hydroxyl group is selected from per se known protective groups. Examples of the protective groups of the hydroxyl group include $C_{1-6}$ alkyl groups (e.g., methyl, tert-butyl, etc.), $C_{6-12}$ aryl groups (e.g., phenyl, naphthyl, biphenylyl, etc.), $C_{7-20}$ aralkyl groups (e.g., trityl, phenylethyl, benzyl, etc.), a formyl group, $C_{1-6}$ alkyl-carbonyl groups (e.g., acetyl, propionyl, etc.), $C_{6-12}$ aryl-carbonyl groups (e.g., benzoyl, naphthylcarbonyl, etc.), $C_{7-20}$ aralkyl-carbonyl groups (e.g., phenylacetyl, phenylpropionyl, etc.), silyl ether type protective groups (e.g., trimethylsilyl, tert-butyldimethylsilyl, tert-butyldiphenylsilyl, etc.), cyclic acetal type protective groups (e.g., tetrahydropyran-2-yl, etc.), alkoxyalkyl groups (e.g., 2-methoxyethoxymethyl, methoxymethyl, etc.), $C_{6-12}$ aryloxy-carbonyl groups (e.g., p-nitrophenoxycarbonyl, etc.), etc.

In the formulas (II), (III), (III'), (III") and (IV),

means that either of the two bonds is a double bond and the other is a single bond. Thus, each of the compounds of these formulas includes a mixture of the resulting two isomers (cis or trans isomers).

In a preferred process embodying the present invention, the dl-tocopherols are produced as follows.

Firstly, the compound (II) (i.e., the compound of the formula (II); hereinafter the compounds of the other formulas are sometimes abbreviated likewise) is reacted with the compound (VI) to give the compound (III').

The amount of the compound (II) to be used is about 0.9 to 1.5 mol, preferably about 1 to 1.2 mol, per mol of the compound (VI).

The reaction is preferably carried out in the presence of a catalyst. Examples of the catalyst include Lewis acids such as zinc chloride, boron trifluoride, aluminium chloride, stannous chloride, etc.; organic acids such as formic acid, acetic acid, p-toluenesulfonic acid, benzenesulfonic acid, etc.; inorganic acids such as sulfuric acid, etc. Lewis acids are preferable. The amount of the catalyst to be used is about 0.5 to 2 mol, preferably about 0.7 to 1 mol, per mol of the compound (VI).

Preferably, the reaction is conducted in an appropriate solvent. Examples of the solvent include hydrocarbons (e.g., toluene, n-hexane, cyclohexane, benzene, xylene, decalin, etc.), ketones (e.g., methyl ethyl ketone, etc.), ethers (e.g., ethyl ether, dioxane, tetrahydrofuran, etc.), esters (e.g., ethyl acetate, ethyl formate, etc.), carboxylic acids (e.g., acetic acid, formic acid, etc.), etc. Ketones are preferable. These solvents can be used alone or a mixture of two or more of the solvents.

The reaction temperature is room temperature to about 180° C., preferably about 60° to 120° C. The reaction time is about 0.5 to 18 hours, preferably about 2 to 6 hours.

In this reaction, in addition to the compound (III'), the compound (IV) is normally produced as a by-product. These products can be used in the next step, if necessary, after purifying them by conventional methods such as distillation under reduced pressure, chromatography, etc.

The compounds (III') and (IV) are novel and have anti-inflammatory activity, antiallergic activity, etc., and are useful as an anti-inflammatory agent, antiallergic agent, hypotensor, myocardiac metabolism-improving agent, etc., as well as an intermediate for the production of dl-tocopherols.

Next, the compound (IV) as the by-product is subjected to ring-closure reaction to give the compound (III"). The mixture of the compounds (III') and (IV) may be subjected to ring-closure reaction to give the mixture of the compounds (III') and (III"). The ring-closure reaction can be carried out by a per se known method (See, e.g., Helvetica Chimica Acta 46, 2517 (1963)). For example, this reaction can be carried out by contacting the compound (IV) or the mixture of the compounds (III') and (IV) with a base. Examples of the base include aromatic tertiary amines such as pyridine, lutidine, collidine, dimethylaniline, etc. Pyridine is preferable. The amount of the base to be used is about 10 to 50 mol, preferably about 20 to 30 mol, per mol of the compound (IV). This reaction may be carried out in a solvent or in the absence of the solvent. Examples of the solvent include the above-mentioned hydrocarbons, ethers, sulfoxides, amides, etc. Preferably hydrocarbons, sulfoxides and amides are used.

The reaction temperature is about 100° to 200° C., preferably about 100° to 120° C. The reaction time is about 4 to 30 hours, preferably about 15 to 25 hours.

Simultaneously with or after the ring-closure reaction, the hydroxyl group may be protected by per se known methods. For example, when the hydroxyl group of the compound (III), i.e., the compound (III') or (III"), is protected by an acyl group, the hydroxyl group can be acylated by per se known methods. The acylating agent used in this reaction includes organic carboxylic acids and their reactive derivatives. The reactive derivatives of the carboxylic acids include acid halides, acid anhydrides, activated amides, activated esters, activated thioesters, etc., each of which can be prepared by conventional methods. Examples of such reactive derivatives are as follows.

1) The acid halides include acid chlorides, acid bromides, etc.

2) The acid anhydrides include symmetrical acid anhydrides, mono $C_{1-6}$ alkyl carbonic mixed anhydrides, mixed acid anhydrides composed of aliphatic carboxylic acids (e.g., acetic acid, pivalic acid, valeric acid, isovaleric acid, trichloroacetic acid, etc.), mixed acid anhydrides composed of aromatic carboxylic acids (e.g., benzoic acid, etc.), etc. Examples of the symmetrical acid anhydrides include $C_{1-6}$ alkylcarboxylic anhydrides such as acetic anhydride, propionic anhydride, butanoic anhydride, etc.

3) The activated amides include carboxylic acid amides with pyrazole, imidazole, 4-substituted imidazole, dimethylpyrazole, benzotriazole, etc.

4) The activated esters include methoxymethyl ester, 1-hydroxybenzotriazole ester, N-hydroxy-5-norbornene 2,3-dicarboxyimide ester, 4-nitrophenyl ester, 2,4-dinitrophenyl ester, trichlorophenyl ester, propargyl ester, ester, etc.; carboxylic acid esters with 1-pentachlorophenyl hydroxy-1H-2-pyridone, N-hydroxysuccinimide, N-hydroxyphthalimide, etc.

5) The activated thioesters include thioesters with heterocyclylthiols (i.e., heterocyclic group - thiol) such as 2-pyridylthiol, 2-benzothiazolylthiol, etc.

The above reactive derivatives can appropriately selected depending on the kind of carboxylic acid.

The acylating agent may be a reactive derivative of a sulfonic acid that can introduce a sulfonic acid acyl group. Examples of such acylating agents include sulfonic acid halides such as methanesulfonyl chloride, benzylsulfonyl chloride, p-toluenesulfonyl chloride, etc.; symmetrical sulfonic anhydrides such as methanesulfonic anhydride, p-toluenesulfonic anhydride, etc.

The amount of the acylating agent such as carboxylic acids, its reactive derivative, reactive derivatives of sulfonic acids, etc., is about 1 to 10 mol, preferably about 1 to 4 mol, per mol of the starting compound (III).

A base is used in the acylating reaction. Examples of the base include tertiary amines such as aliphatic tertiary amines (e.g., triethylamine, etc.), aromatic tertiary amines (e.g., pyridine, α-, β- or γ-picoline, 2,6-lutidine, 4-dimethylaminopyridine, 4-(1-pyrrolidinyl)pyridine, dimethylaniline, diethylaniline, etc.), organic acid salts (e.g., sodium acetate, etc.), etc.

The amount of the base to be used is normally about 1 to 100 mol, preferably about 1 to 5 mol, per mol of the starting compound (III).

This reaction is carried out in a solvent that does not hinder the reaction or in the absence of a solvent. Examples of the solvent that does not hinder the reaction include ketones such as acetone, etc.; ethers such as diethyl ether, isopropyl ether, tetrahydrofuran, dioxane, etc.; carboxylic acids such as acetic acid, propionic acid, etc.; nitriles such as acetonitrile, etc.; hydrocarbons such as benzene, toluene, xylene, etc.; halogenated hydrocarbons such as dichloromethane, chloroform, 1,2-dichloroethane, etc.; esters such as ethyl acetate, etc.; amides such as dimethylformamide, dimethylacetamide, etc.; tertiary amines such as triethylamine, tributylamine, N-methylmorpholine, N-methylpiperidine, N,N-dimethylaniline, etc.; pyridine and its derivatives such as picoline, lutidine, collidine, etc. These solvents can be used alone or a mixture of two or more of the solvents in an appropriate mixing ratio.

The reaction temperature is not specifically limited, but is normally about −30° to 100° C., preferably about 10° to 50° C. The reaction time is about several minutes to scores of hours, for example, about 5 minutes to 30 hours.

For example, the hydroxyl group can be protected with an acetyl group by reacting the compound (III) with an acetic acid derivative (e.g., acetic anhydride, acetyl chloride, etc.) in a base (e.g., pyridine, triethylamine, etc.). The amount of the acetic acid derivative to be used is about 1 to 10 mol, preferably about 2 to 5 mol, per mol of the compound (III). The hydroxyl group can be protected with a methoxyethoxymethyl group by reacting the compound (III) with methoxyethoxymethyl chloride in the presence of a base (e.g., triethylamine, etc.). The amount of the methoxyethoxymethyl chloride to be used is about 1 to 5 mol, preferably about 1.2 to 2 mol, per mol of the compound (III). Preferred examples of the solvent include the above-mentioned ethers, hydrocarbons, halogenated hydrocarbons, amides, etc.

The compound (III) thus obtained can be used in the next step as the reaction mixture or crude product, or after purifying it by per se known methods (e.g., concentration, extraction, chromatography, distillation, etc.).

The compound (III) thus obtained is novel and has antioxidizing activity, and is useful as an antioxidant in foods, feeds, medicaments, etc., as well as an intermediate for the production of dl-tocopherols.

Next, the compound (III) obtained in the above reaction is subjected to reduction reaction to give the desired compound (V). The reduction can be carried out by per se known methods such as catalytic hydrogenation. The catalytic hydrogenation is carried out by introducing hydrogen gas into the reaction mixture in an appropriate solvent in the presence of a catalyst.

Examples of the solvent include alcohols (e.g., methanol, ethanol, isopropanol, etc.), carboxylic acids (e.g., acetic acid, etc.), hydrocarbons (e.g., hexane, cyclohexane, benzene, toluene, xylene, etc.), ethers (e.g., tetrahydrofuran, dioxane, isopropyl ether, etc.), etc. Alcohols are preferred. These solvents can be used alone or a mixture of two or more of the solvents.

Examples of the catalyst include platinum (e.g., platinum oxide, hexachloroplatinic (IV) acid, etc.), palladium, rhodium, luthenium, nickel (e.g., Raney nickel, etc.), and copper-chromium catalyst. Palladium is preferred. The catalyst may be adsorbedon carriers. Examples of such carriers include activated charcoal, alumina, barium sulfate, calcium carbonate, strontium carbonate, etc. The amount of the catalyst to be used is about 0.01 to 0.1 mol, preferably about 0.015 to 0.020 mol, per mol of the compound (III') or (III").

The reaction temperature is about 10° to 100° C., preferably about 10° to about 60° C. The reaction time is about 0.5 to 5 hours, preferably about 1 to 2 hours. The hydrogen pressure is about 1 to 10 atm, preferably about 1 to 3 atm.

The protective group of the resulting compound (V) can be removed by per se known methods. For example, an alkyl group, aryl group, aralkyl group, acyl group, silyl ether type protective group, or cyclic acetal type protective group as the protective group can be removed by subjecting the compound (V) to hydrolysis with an alkali (e.g., sodium hydroxide, potassium hydroxide, etc.) or an acid (e.g., hydrochloric acid, sulfuric acid, etc.) in water or aqueous alcohol (e.g., methanol, ethanol, etc.). A methoxyethoxymethyl group as the protective group can be removed by treating the compound (V) with anhydrous zinc bromide in a halogenated hydrocarbon (e.g., methylene chloride, etc.).

The desired compound (V) obtained by the process of the present invention can be isolated or purified by per se known separation and purification means such as filtration, concentration, solvent extraction, solvent conversion, redistribution, crystallization, recrystallization, chromatography, distillation under reduced pressure, etc. For example, the compound (V) can be purified by filtering the reaction mixture, concentrating the filtrate, and subjecting the residue to chromatography.

The compound (V) thus obtained has, for example, antioxidizing activity, and can be used as food or feed additives or in medicaments.

The compound (II) used as the starting compound in the process of the present invention can be prepared by reacting the compound of the formula (I):

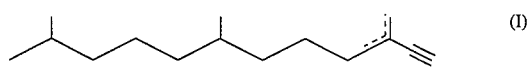

wherein

means that either of the two bonds is a double bond and the other is a single bond, with 2-methyl-2-vinyloxirane.

The amount of 2-methyl-2-vinyloxirane to be used is about 1 to 3 mol, preferably about 1 to 1.2 mol, per mol of the compound (I).

The reaction is usually conducted in an appropriate solvent. Examples of the solvent include ethers (e.g., tetrahydrofuran, dioxane, isopropyl ether, etc.), sulfoxides (e.g., dimethyl sulfoxide, etc.), amides (e.g., N-,N-dimethylformamide, etc.), hydrocarbons (e.g., benzene, toluene, xylene, etc.), etc. These solvents can be used alone or as a mixture of two or more of the solvents.

The reaction temperature is about −78° to 100° C., preferably room temperature to about 70° C. The reaction time is about 1 to 10 hours, preferably about 1 to 4 hours.

The compound (I) may be readily produced by a known synthesis method.

The compound (II) thus obtained can be used for the starting compound of the process of the present invention as the reaction mixture or crude product, or after separation or purification by per se known methods (e.g., solvent extraction, concentration, chromatography, distillation, etc.).

As described above, the present invention provides a process for producing dl-tocopherols. The process of the present invention readily produces dl-tocopherols in high yield through a few steps from inexpensive industrial starting material.

In addition, the present invention provides novel compounds useful as intermediates for the above process. Some of these novel compounds have pharmacological activity and are useful as medicaments as well as the intermediates for the above process.

The following examples further illustrate the present invention in detail but are not to be construed to limit the scope thereof. In the examples, all the percent (%) is percent (%) by weight unless otherwise indicated.

EXAMPLE 1

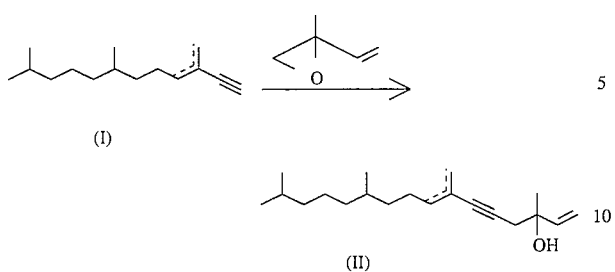

60% Sodium hydride (in oil) (0.2 g) was suspended in isopropyl ether (4 ml). A solution of 3,7,11-trimethyl-3-dodecen-1-yne (the compound (I))(1 g) (a mixture of 3,7,11-trimethyl-3-dodecen-1-yne and 7,11-dimethyl-3-methylene-dodeca-1-yne which were prepared according to the scheme described at page 3 of the present specification, i.e. by the method described in JP-B 38-26657) in isopropyl ether (4 ml) was added dropwise to the suspension. Tetrahydrofuran (THF)(2 ml) and dimethyl sulfoxide (DMSO)(1 ml) were added, and a solution of 2-methyl-2-vinyloxirane (0.42 g) in isopropyl ether (2 ml) was added dropwise. The mixture was warmed slowly from room temperature, and stirred at 60° to 70° C. for 4 hours. The reaction mixture was cooled, saturated brine was added to separate the mixture into layers. The aqueous layer was extracted with isopropyl ether. The isopropyl ether layer was dried over sodium sulfate and concentrated to give crude product. The crude product was purified by silica gel column chromatography (n-hexane: ethyl acetate=10:1 v/v) to give 3,7,11,15-tetramethyl-1,7-hexadecadien-5-yn-3-ol (the compound (II))(580 mg). The unreacted compound (I) (510 mg) was recovered. The structure of the desired product was confirmed by NMR analysis.

NMR (CDCl$_3$) TMS δ: 0.90(s,3H), 0.97(s,3H), 1.10–2.40(m,16H), 1.43(s,3H), 2.60(m,2H), 5.10–5.50(m, 3H), 5.90–6.30(m,H).

EXAMPLE 2

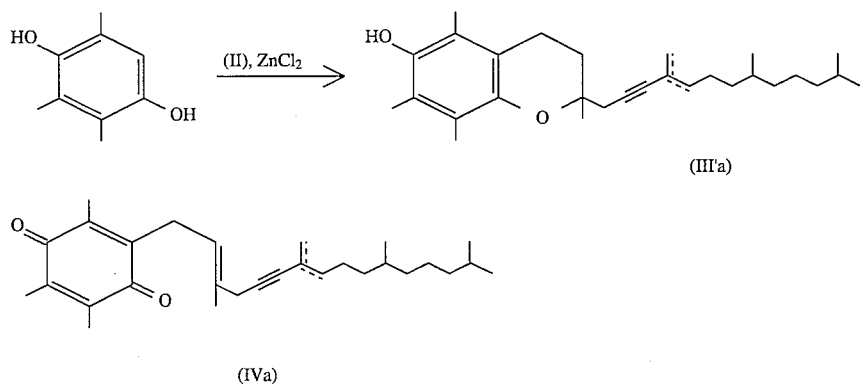

A mixture of trimethylhydroquinone (0.87 g), toluene (2 ml), methyl ethyl ketone (0.5 ml), acetic acid (0.03 ml) and anhydrous zinc chloride (ZnCl$_2$)(0.6 g) was heated to 100° C. A solution of the compound (II)(2 g) in toluene (1 ml) was added dropwise over 20 minutes to the mixture, and the resulting mixture was stirred for 5 hours. The reaction mixture was cooled, extracted with toluene, washed with water, dried over sodium sulfate, and concentrated to give the crude product. The crude product was separated and purified by silica gel column chromatography to give 2,5,7,8-tetramethyl2- (4',8',12'-trimethyl-4'-tridecen-2'-yne)-6-chromanol (the compound (III'a)) (0.77 g) and 3,5,6-trimethyl-2- (3',7',11',15'-tetramethyl-2',7'-hexadecadien-5'-yne)-1,4-benzoquinone (the compound (IVa)) (1.57 g). The structures of the compounds were confirmed by NMR analysis.

The compound (IVa): NMR (CDCl$_3$) TMS δ: 0.80(s,3H), 0.90(s,6H), 0.90–1.70(m,14H), 1.70–1.85(m,6H), 2.00(s, 9H), 2.85–3.03(broad,2H), 3.10–3.30(broad,2H), 4.90–5.70(m,3H).

The compound (III'a): NMR (CDCl$_3$) TMS δ: 0.80(s,3H), 0.90(s,6H), 1.20(s,3H), 1.95(s,6H), 2.10(s,3H), 1.00–3.00(m,20H), 4.20(s,H), 5.10–5.30(broad,2H).

EXAMPLE 3

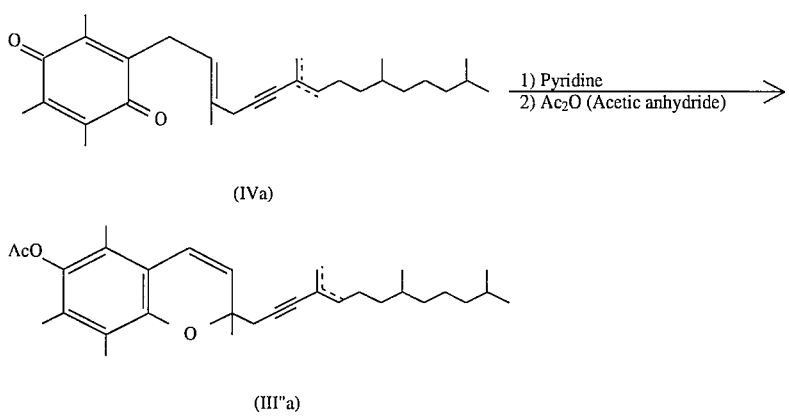

The compound (IVa)(1.57 g) was dissolved in pyridine (10 ml), and the mixture was refluxed in nitrogen gas for 24 hours. Acetic anhydride (4 ml) was added, and the mixture was stirred at about 100° C. for 3 hours for acetylation. The reaction mixture was concentrated, and the residue was extracted with ethyl acetate, washed with water, and dried over sodium sulfate. Evaporation of the solvent gave a crude product. The crude product was purified by silica gel column chromatography (n-hexane: ethyl acetate=99:1) to give 6-acetoxy-2,5,7,8-tetramethyl-2-(4',8',12'-trimethyl-4'-tridecen-2'-yne)-2H-chromene (the compound (III"a)) (1.26 g) as an oil. The structure of the compound was confirmed by NMR analysis.

NMR (CDCl$_3$) TMS δ: 0.87(s,3H), 0.93(s,6H), 1.10–1.70(m,13H), 1.57 (s,3H), 1.80(d,2H,J=6Hz), 2.07(s, 6H), 2.15(s,3H), 2.35(s,3H), 2.63–2.83(m,2H), 5.23(d,H, J≈6Hz), 5.80(d,H,J≈10.5Hz), 6.60(d,H,J≈10.5Hz).

EXAMPLE 4

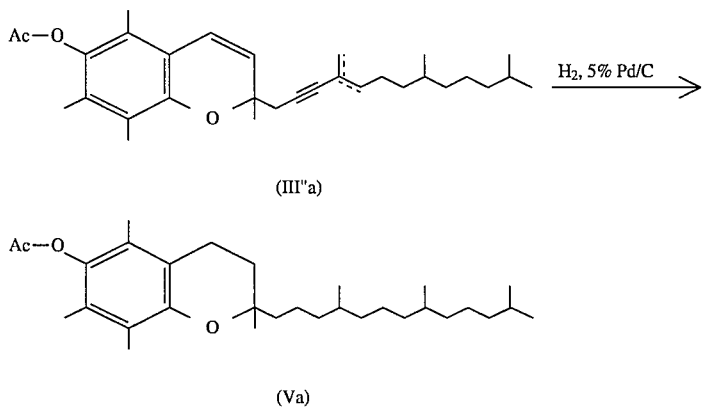

The compound (III"a) (1.2 g) was dissolved in ethanol (70 ml). 5% Palladium-carbon (Pd/C)(0.1 g) was added to the solution, and reduction was carried out with hydrogen gas (3.0 kg/cm$^2$) at room temperature for 2 hours. The reaction mixture was filtered, and the filtrate was concentrated. The crude product was purified by silica gel column chromatography (n-hexane: ethyl acetate=99:1) to give 6-acetoxy-2,5,7,8-tetramethyl-2-(4',8',12'-trimethyltridecyl) chromane (the compound (Va)) (0.98 g).

NMR (CDCl$_3$) TMS δ: 1.80–1.87 (Mex4), 1.20 (Me), 1.00–1.60(m,21H), 1.75(t,2H,J=6Hz), 1.95(s,3H), 2.00(s, 3H), 2.07(s,3H), 2.30(s,3H), 2.60(t,2H,J=6Hz).

What is claimed is:

1. A process for producing a compound of the formula (II):

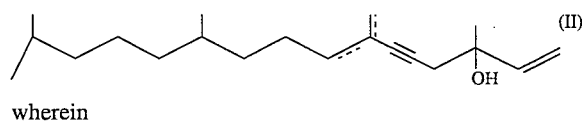

wherein

means that either of the two bonds is a double bond and the other is a single bond, which comprises reacting a compound of the formula (I):

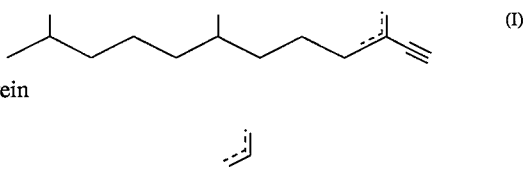

wherein

is as defined above, with 2-methyl-2vinyloxirane.

* * * * *